United States Patent [19]

Liston et al.

[11] Patent Number: 4,477,190
[45] Date of Patent: Oct. 16, 1984

[54] MULTICHANNEL SPECTROPHOTOMETER

[75] Inventors: Max D. Liston, Irvine; David G. Dickinson; William A. Stark, both of Costa Mesa, all of Calif.

[73] Assignee: American Hospital Supply Corporation, Evanston, Ill.

[21] Appl. No.: 284,841

[22] Filed: Jul. 20, 1981

[51] Int. Cl.³ .................................................. G01J 3/50
[52] U.S. Cl. ..................................................... 356/418
[58] Field of Search ................ 356/409, 414, 418, 419, 356/420, 433, 434, 435

[56] References Cited

U.S. PATENT DOCUMENTS

| | | | |
|---|---|---|---|
| 3,697,185 | 10/1972 | Kassel et al. | 356/418 |
| 3,833,304 | 9/1974 | Liston | 356/418 |
| 3,963,351 | 6/1976 | Chance et al. | 356/418 |
| 4,004,150 | 1/1977 | Natelson | 356/434 |
| 4,061,428 | 12/1977 | Amano et al. | 356/418 |

FOREIGN PATENT DOCUMENTS 125436  9/1980  Japan .................................. 356/414

Primary Examiner—Vincent P. McGraw
Attorney, Agent, or Firm—Michael P. Bucklo; John H. Faro

[57] ABSTRACT

A multichannel spectrophotometer has a single radiant energy source formed into a multiplicity of radiant energy beams which are each simultaneously intercepted by segments of a rotary source filter wheel, the spectral radiant energy output selected by each filter segment being directed into a separate source radiant energy conduit and transmitted to a remote sample station where a cuvette containing a sample to be analyzed is located, the radiant energy outputs of each cuvette being directed into a separate detector radiant energy conduit where each conduit is intercepted by a filter segment of a second rotating detector filter wheel identical to the source filter wheel and rotated in aligned synchronism therewith, the spectral radiant energy outputs of each segment of the detector filter wheel being further directed into a separate radiant energy detector and signal processing electronics associated with that sample station or spectrophotometer channel from which the radiant energy signal being detected and analyzed has been received. Central control, timing and display electronics are shared by each channel and may be overall programmed and controlled by computer. In one application involving the measurement of fluorescence, the filters of the detector filter wheel will be different from the filters of the source filter wheel so as to excite the sample cuvette at one wavelength and to measure fluorescent response at another.

10 Claims, 6 Drawing Figures

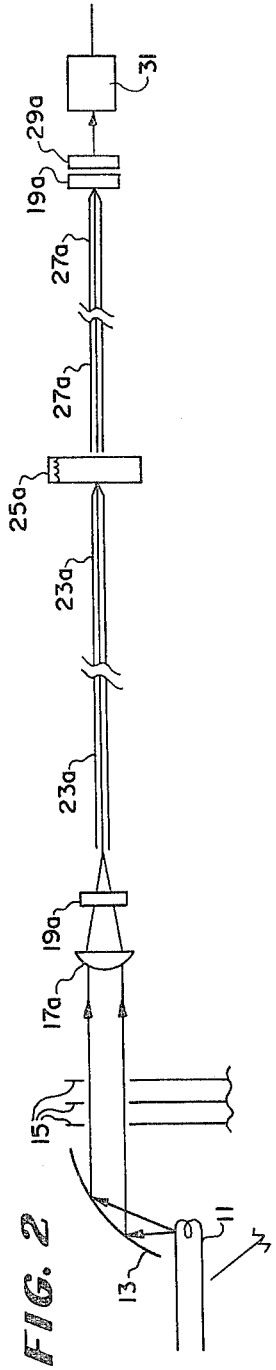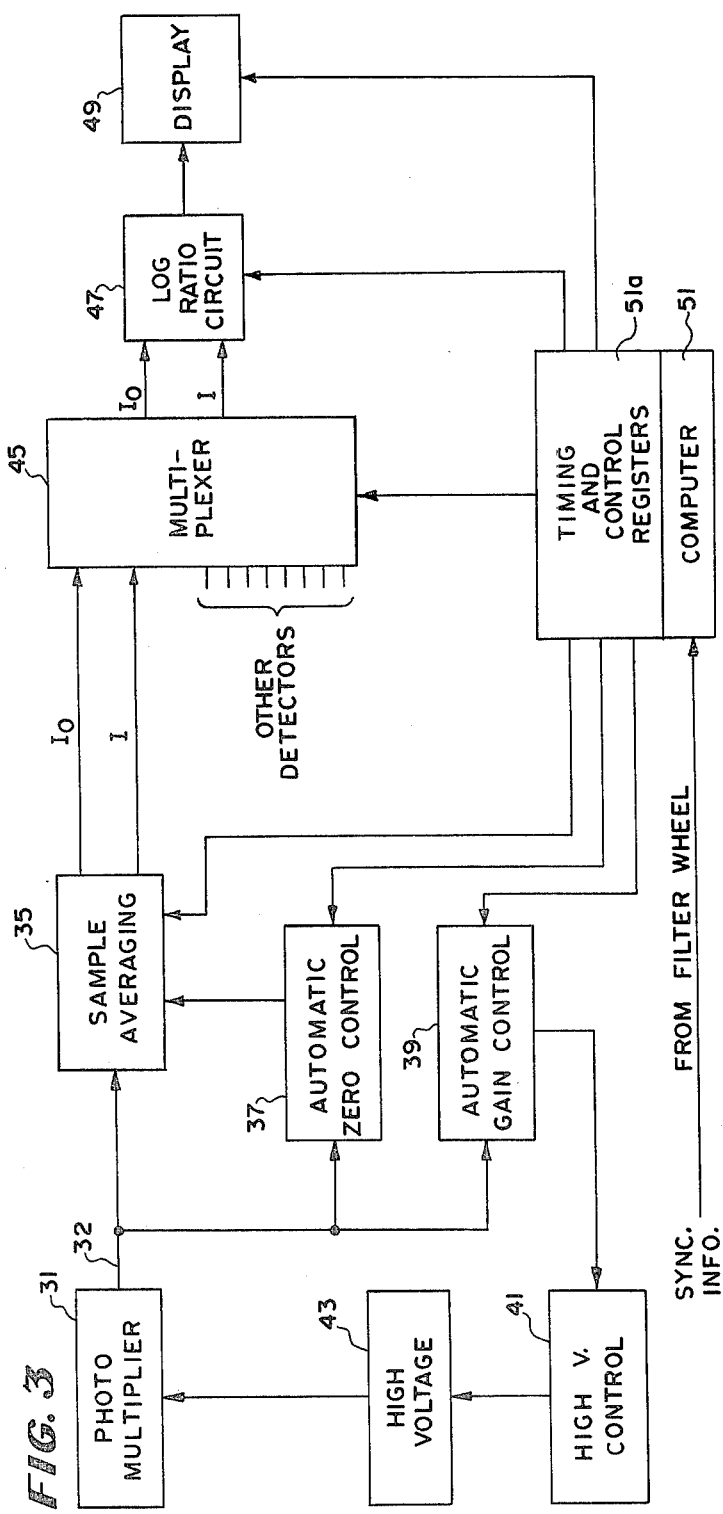

MULTICHANNEL SPECTROPHOTOMETER

The present invention relates to spectrophotometers and more particularly to spectrophotometers for blood chemistry analysis.

In the field of spectrophotometers, it has been the general practice to employ a source of radiant energy along with spectral selective elements to produce a single channel for measurement of spectral responses of samples to be measured. Multichannel spectrophotometers have been assembled using a common source of radiant energy with separate spectral selective elements to determine the spectral sensitivity of each channel. If a multiplicity of channels are required such as in blood chemistry analysis, the less common elements per channel, the more expensive and costly each channel becomes. Also, it becomes necessary to wait for a particular channel to become available to use its region of spectral interest for other measurements. Since the greatest application for multichannel spectrophotometers is in blood chemistry analysis, waiting can cause considerable delay in completing all the tests required on a given blood sample. In this general field of application, the spectrophotometers define the spectrum of interest by a single narrow band filter usually associated with the input to the radiant energy detector. Although such devices have served the purpose, they have not proved entirely satisfactory under all conditions of service for the reasons outlined above and furthermore, unless complete duplicate filter systems are provided only one at a time measurements at a given wave length can be measured or there is filter sharing or switching. These problems are overcome by the present invention.

In another analyzer, the system whirls the samples, contained in thirty cuvettes arranged around the periphery of a rotating disk. As the rotor picks up speed the centrifugal force transfers reagents from an inner disc to the cuvettes, which have transparent tops and bottoms. The chemical reactions are measured "on the fly" as the cuvettes containing the sera being measured pass through a beam from a common source lamp mounted at the top of the apparatus. The beam is spectrally filtered for the proper measurement at each detector. The rotor is timed so that the exposure of each chemical reaction in the light beam is long enough that its absorbance peak can be measured, yet is short enough to track the thirty kinetic reactions in real time.

Those concerned with the development of clinical blood analyzers have long recognized the need for a multichannel spectrophotometer which can be simultaneously utilized to measure the results at a multiplicity of sample stations. The present invention fulfills this need.

One of the most critical problems concerning designers of multichannel spectrophotometers has been the ability to easily and simply limit and define the spectral areas of sensitivity of each channel and to eliminate the problems of stray interfering radiant energy. The present invention fulfills this need.

The general purpose of this invention is to provide a multichannel spectrophotometer which embraces all the advantages of similarly employed spectrophotometer devices and possesses none of the aforedescribed disadvantages. To attain this the present invention contemplates a unique dual rotating filter wheel assembly, one on the source and one on the detector sides of the sample, whereby the effects of stray light and poor spectral selectivity are avoided.

An object of the present invention is the provision of a spectrophotometer containing a multiplicity of channels which can make bichromatic measurements substantially at the same time.

Another object is to provide a multichannel spectrophotometer which shares identical source and detector filter wheels which are aligned and rotate in synchronism.

Still another object of the present invention is to provide a multichannel spectrophotometer which makes measurements at a multiplicity of test stations simultaneously.

Still another object of the present invention is to provide a multichannel spectrophotometer which spectrally filters the radiation both before and after the sample cuvette.

Other objects and many of the attendant advantages of this invention will be readily appreciated as the same become better understood by reference to the following detailed description when considered in connection with the accompanying drawings in which like reference numerals designate like parts throughout the figures thereof and wherein:

FIG. 2 shows the optical path of one of the channels of the multichannel spectrophotometer illustrated in FIG. 1;

FIG. 3 illustrates a block diagram of the timing, control and display electronics associated with each channel of the spectrophotometer;

Figure 1:
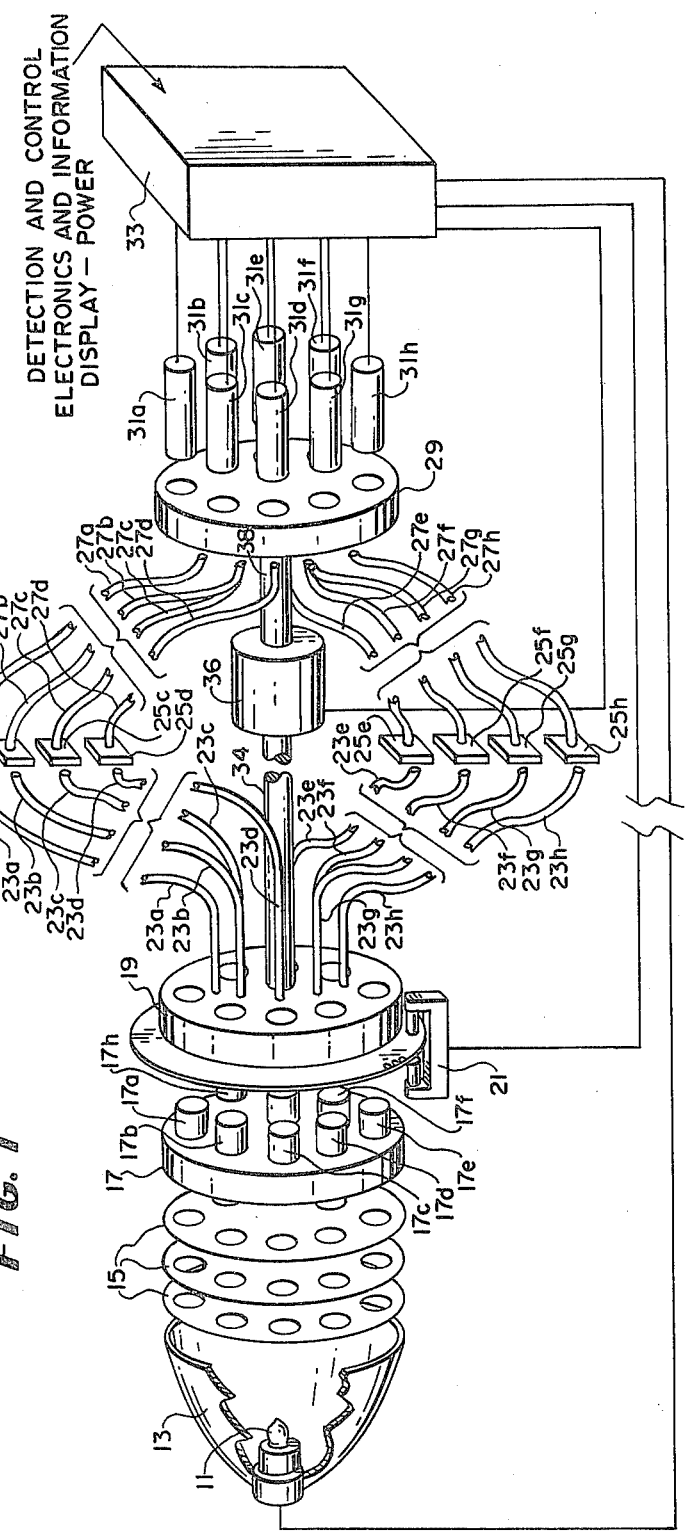
FIG. 1 illustrates an exploded end perspective view of a preferred embodiment of the invention.

Referring now to the drawings, wherein like reference characters designate like or corresponding parts throughout the several views, there is shown in FIG. 1 a lamp 11 centered in a parabolic reflector 13. The electromagnetic radiant energy from lamp 11 is reflected from parabolic reflector 13 through heat baffles 15 to a lens disk 17. Heat baffles 15 have a circular pattern of circular holes cut near the periphery thereof to form a multiplicity of radiant energy beams from the energy reflected by parabolic reflector 13 from lamp 11. Lens disk 17 contains a series of lenses and mountings 17a–17h mounted around the outer edge thereof and aligned with the circular holes of heat baffles 15. These lens assemblies collect and direct the electromagnetic energy from lamp 11 and heat baffles 15 through rotating filter wheel 19 into electromagnetic energy conduits or light pipes 23a through 23h. An optical encoder 21 identifies the filter wheel positions so that the different filters arranged in a circular pattern along the periphery of the filter wheel are identified and known by the position of the wheel. Each lens of the lens assembly 17a–h focuses its electromagnetic energy beam on a respective light pipe 23a–h where each light pipe then transmits its corresponding selected spectrum of energy to a cuvette 25a–h for transmission therethrough. The spectral radiant energy outputs of each of the cuvettes is transmitted into a respective detector electromagnetic energy conduit 27a–h where these detector light pipes or electromagnetic energy conduits 27a-h direct their energy, respectively, through a detector filter wheel 29 which is identical with source filter wheel 19. Filter wheel 19 is connected by a shaft 34 to a synchronous motor 36 which also is connected by shaft 38 to filter wheel 29. The output of each filter segment of detector filter wheel 29 is directed to photodetectors 31a-h. Each photodetector is connected to electronic section 33 where the signals are detected and processed for display. Since source filter wheel 19 and detector filter wheel 29 are identical as far as filter segments are concerned and rotate in aligned synchronism, optical encoder then informs electronics 33 of the exact position of each filter on each wheel at any point in time.

It should be noted that one of the positions in the filter wheel is a blank and has zero transmission. This segment is used to establish the zero reference for the automatic zero circuitry discussed hereinbelow.

It should be further noted that lamp 11 may be a quartz halogen lamp made by Ushio Inc. such as JA 12V 55 WD, and electromagnetic energy conduits 23, 25 and 27 may be quartz fibers or other suitable optic material, or may be a light pipe or tube containing a transmission material of suitable optical index to contain the radiant energy therewithin.

The filters utilized on the filter wheels are very narrow band pass interference filters having band widths of 8 nm. The nano-meter wave lengths chosen for the particular filter spectral bands for blood measurement application are as follows: 340 nm, 405 nm, 450 nm, 525 nm, 550 nm, 575 nm, and 630 nm.

Although identical source and detector filter wheels are described above having the same filters in the same corresponding positions, it is contemplated within this invention that the detector filter segments can be different from the source filter segments for the purposes of certain measurements involving fluorescence where the sample cuvette is excited by electromagnetic radiation at one wavelength and the fluorescent response is measured at another. Therefore the description of FIG. 1 is to include this application where the filter wheels are rotated in synchronism but are not identical in wavelength.

In FIG. 2, there is illustrated the optical path of the electromagnetic energy of one of the beams of the preferred embodiment illustrated in FIG. 1. Electromagnetic energy emitted from lamp 11 is reflected from parabolic reflector 13 through heat baffles 15 and into a plano convex lens 17a where the energy is focused through filter 19a into source electromagnetic energy conduit 23a or light pipe 23a. The electromagnetic energy transmitted by light pipe 23a is transmitted through cuvette 25a containing a sample to be analyzed and then into detector electromagnetic energy conduit or light pipe 27a and through a neutral filter 19a and band-pass filter 29a which is identical with filter 19a, except for fluorescence measurement, and finally into photo-detector 31a. It should be noted that photodetector 31 may be of the photo multiplier type, which has a high sensitivity and a large dynamic range such as Hamamatsu photo-multiplier tube number R6487647. Since the narrow-band filters are sensitive to temperature, air is blown through heat baffles 15 (not illustrated) to control the temperature of filter wheel 19 In addition, the photo-multiplier tubes are also temperature sensitive wih respect to their spetral response and it is therefore desirable to control the temperature thereof by appropriate means. FIG. 3 illustrates a block diagram of the electronics associated with each channel of the multichannel spectrophotometer embodiment of FIG. 1. Photomultiplier 31 is connected by line 32 to a sample averaging block 35, an automatic zero block 37 and an automatic gain control block 39. Each of these blocks are under the control of timing and control registers 51a and a computer 51. Sample averaging block 35 may be a simple integrating circuit timed to receive the signal pulses from the desired channel to which photomultiplier 31 is connected and to integrate these pulses to improve the signal to noise ratio. One of the integrated signals, Io, which is the reference signal produced by the signal pulse at the desired reference wave length and the other integrated signal is I which is the sample signal produced by the pulses at the sample wave length. These are selected gates operated by the appropriate timing and control registers as the filter wheels rotate in the multichannel spectrophotometer.

The automatic zero control for a given channel is operated every time the non-transmitting or blank segment of the filter wheel is opposite photomultiplier 31 of the given channel. It establishes a reference voltage which is used to cancel the voltage measured during the filter blank thereby establishing a "true" zero when there is no input signal.

Automatic gain control 39 adjusts the gain of each photomultiplier depending upon the amplitude of the first few signal pulses received in that channel. These first few pulses are received and integrated and a voltage established which is connected to a high voltage control 41 to adjust a high voltage power supply 33 to raise or lower the high voltage on the photomultiplier to change its gain. Since the dynamic range of the pulses may vary as much as 1000 to 1, it is necessary to adjust the gain of the photo multiplier to accommodate this dynamic range.

The reference and sample output signals I and Io are fed into a multiplexer 45 along with the similar sample and reference signals from other channels to be alternately switched into a log ratio circuit 47. This circuit is described in detail in U.S. Pat. No. 3,664,744 entitled "Log Ratio Circuit For Double Beam Spectrophotometers" granted to this inventor May 23, 1972. The output of log ratio circuit 47 which now provides a signal related to the concentration of the unknown being measured, is connected to a display 49 which may be a hard copy machine or one of a variety of alph-numeric displays well known to the electronic designer.

It should be noted that computer 51 may be part of an overall computer system along with other pieces of measurement and control equipment of which the multichannel spectrophotometer is a part. Programs in the computer can be utilized to make the multichannel spectrophotometer a useful integral part of an overall measurement system or large clinical analyzer. The sync information from the source filter wheel enables the computer to know at all times the position of a given filter and the identification signal pulses appearing in any given channel.

Figure 4:
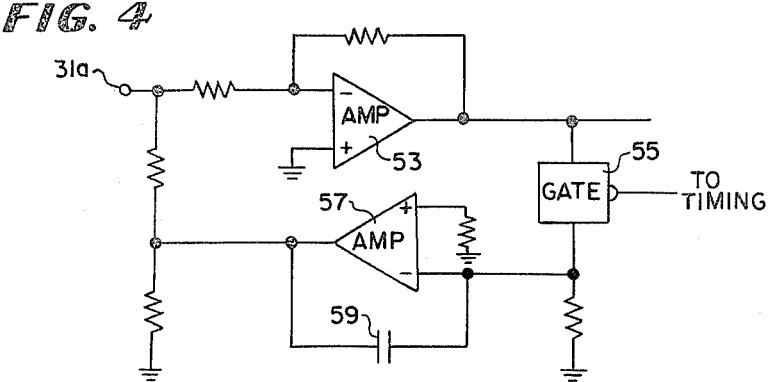
FIG. 4 shows the automatic zero control circuitry of FIG. 3.

In FIG. 4, there is illustrated the circuit details of automatic zero control 37 consisting of an operational amplifier 53 whose output is connected by a gate 55 to an integrating amplifier 57 consisting of an operational amplifier with an integrating capacitor 59. When a blank in each filter wheel comes in position for a particular channel, gate 55 is opened to transmit whatever voltage offset appears at the output of amplifier 53 for that channel and it is stored on capacitor 59 and held as an offset voltage which is applied back to the input of operational amplifier 53 to offset any voltage when the blank appears in the filter wheel for that channel.

Figure 5:
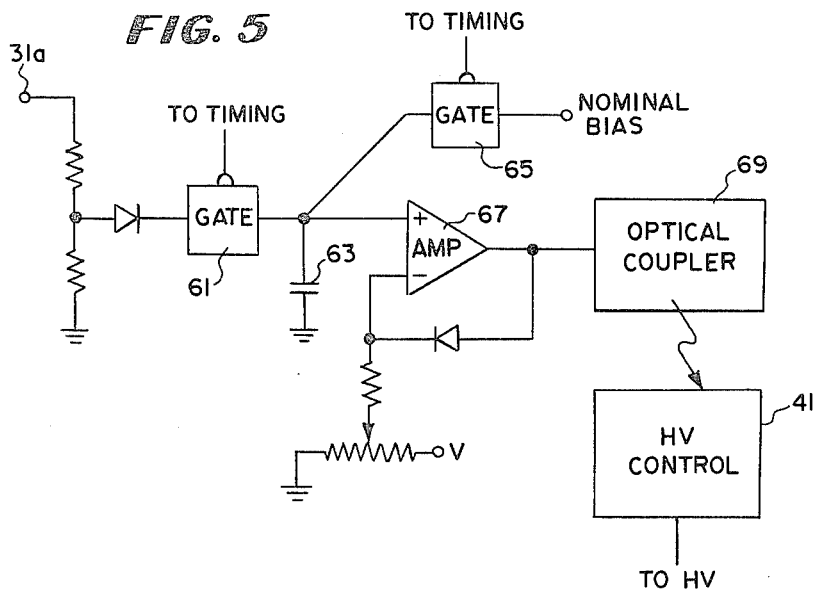
FIG. 5 illustrates the circuit details of the automatic gain control circuitry of FIG. 3.

FIG. 5 illustrates the circuit details of automatic gain control 39 of FIG. 3. A capacitor 63 is connected through gate 61 through a resistor network to line 32. Capacitor 63 is also connected through a gate 65 to a nominal bias. Capacitor 63 is further connected to the input to operational amplifier 67 whose output is connected to optical coupler 69 which optically couples a control signal to high voltage control 41. As gate 61 is operated to connect the first few pulses from the photomultiplier detector, voltage across capacitor 63 is changed changing the output voltage of amplifier 67 which in turn is coupled by optical coupler to high voltage control 41. Therefore, if the pulses are extremely large, the gain on the photomultiplier tube for that channel can be reduced to accommodate the large pulses and prevent overload of the analog circuits. This allows the photomultiplier detector to accommodate the extreme dynamic range experienced by the different spectrophotometer channels. Gate 65 enables the gain to be quickly returned to normal range from an extreme by gating a normal voltage to capacitor 63.

Figure 6:
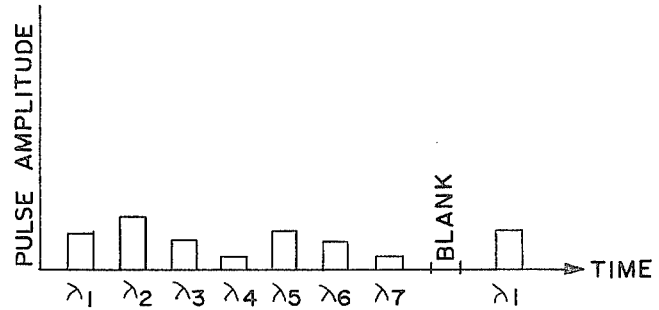
FIG. 6 illustrates the typical pulse train received through the filter wheel system at the photodetector output.

FIG. 6 illustrates the sequence of pulses which may be generated at the photomultiplier output of each spectrophotometer channel. For example, the averaging circuit 35 of FIG. 3 may average 100 pulses of wave length lambda$_2$ or the second pulse of FIG. 6 to obtain the signal value which will be used for that channel. Similarly, the same averaging is utilized to obtain the reference signal.

Operation of the preferred embodiment illustrated in FIG. 1 may be described first by reference to FIGS. 1 and 2. Lamp 11 with parabolic reflector 13 and heat baffles 15 along with lens disk 17 and lens assemblies 17a–h, form light substantially parallel beams of wide band electromagnetic radiant energy. Heat baffles 15 are required since the interference filters used in rotating filter wheel 19 are sensitive to temperature, each segment of filter wheel 19 containing an interference filter having a narrow spectral band centered at a given wave length as hereinbefore set forth. Therefore, except for the blank segment of the filter wheel, each "light pipe" 23a–h transmits a narrow band of electromagnetic energy centered at the wave length of the filter oppositely disposed that particular light pipe at that moment. The filter wheel makes 30 revolutions per second and therefore every second each light pipe 23a–23h sees repeatedly at 30× per second a sequential series of seven narrow bands of spectral energy and a blank reference. Light pipes 23a–h transmit this successive series of narrow bands of spectral energy to eight different test stations containing a sample cuvettes 25a–h to be analyzed. If the cuvettes contain blood serum to be analyzed, the various filters for the filter wheel will be chosen to perform the various tests required. For each test one wave length will be chosen as a reference and another as the sample wave length or bichromatic. Once these tests and wave lengths are established, then the filters can be selected for the filter wheel.

Cuvettes a–h may be part of an overall system of blood analysis and can be part of a continuous chain of cuvettes which are moved in a controlled environment from one test station to another.

The energy from cuvettes 25a–h, respectively, is directed into detector light pipes 27a–h. To prevent stray radiant energy from interfering with the desired signals and to increase the spectral selectivity of the system the detector light pipes direct their energy through a second rotating filter wheel 29 having the same identical filters as filter wheel 19 and the same identical positions. Consequently when light pipe 23a is receiving output from filter lambda one, then detector 31a is receiving energy from filter lambda one directed thereto by detector light pipe 27a. To balance the energy transmission in each of the transmission paths, FIG. 2 illustrates the use of a neutral filter 29a. Neutral filter 29a has no spectral characteristics and attenuates the energy transmitted therethrough. It merely balances or attempts to balance the flat spectral energy transmission from path to path.

It should be noted although quartz fiber optics is desired for light pipes 23 and 27, other forms of electromagnetic energy transmission conduits may be utilized. Conduits containing various liquids have proved successful and may be preferred over fiber optics under certain circumstances.

Therefore, the output of each photomultiplier detector 31 appears much as the train of pulses illustrated in FIG. 6 where the sequence repeats and repeats as the filter wheel rotates and completes each resolution.

Turning now to FIG. 3, since the filter wheels rotate at 1800 revolutions per minute, in 3 and ⅓ pulse samples are averaged by sample averaging 35 to produce an Io reference and an I sample signal from each channel. There being a sample averaging circuit 35 for each photomultiplier detector 31a–h, the concentration of the unknowns being measured for each of the channels is computed by the log ration circuit 47 shared by all the channels through multiplexer 45 and displayed by display 49.

The automatic gain control and zero control which have been previously discussed make the multichannel spectrophotometer ideally suited to blood chemistry measurements.

Although not illustrated, it should be emphasized that the temperature of the filter wheels must be controlled in order to preserve the spectral characteristics of the interference filters. Typical fans and blowers under reasonable temperature control are sufficient for this task.

It should be quite evident that the multichannel spectrophotometer can be placed under computer control and to have the desired sequence of measurements to be performed at the remote cuvette stations merely by programming the computer to operate the timing and control registers in a manner which gate the appropriate pulses into the proper electronic sections at the proper time. Therefore the multichannel spectrophotometer is completely adaptable to automatic control including test sequences, tests to be performed at various locations and data handling, processing and display.

It now should be apparent that the present invention provides a mechanical and circuit arrangement which may be employed in conjunction with a multichannel spectrophotometer for providing a highly spectrally sensitive instrument to perform a variety of tests at remote test stations.

Although particular components, etc. have been discussed in connection with a specific embodiment of a spectrophotometer constructed in accordance with the teachings of the present invention, others may be utilized. Furthermore, it will be understood that although an exemplary embodiment of the present invention has been disclosed and discussed, other applications of circuit arrangements are possible and that the embodiments disclosed may be subjected to various changes, modifications and substitutions without necessarily departing from the spirit of the invention.

What is claimed is:

1. A spectrophotometer for the simultaneous measurement of the transmission characteristics of a multiplicity of samples at selected spectral wave lengths comprising:

a single radiant energy source;

optical means for forming said single radiant energy source into a circular pattern of a multiplicity of substantially parallel beams of radiant energy;

a source filter wheel, having a multiplicity of spectrally selective filters arranged in a circular pattern substantially matching the circular pattern of said optical means, said source filter wheel and said filters thereon being positioned and arranged such that each filter sequentially receives and selectively transmits spectral portions of each one of the multiplicity of beams as said source filter wheel is rotated;

means for rotating said source filter wheel;

a multiplicity of source radiant energy conduits, one end of each source conduit being oppositely disposed one of said multiplicity of beams of radiant energy such that as said source filter wheel rotates each filter of said source filter wheel passes and intercepts each beam and transmits into each respective source conduit the spectrum associated with that filter for transmission through a sample cuvette;

a multiplicity of sample cuvettes, each one located at the other end of one of said multiplicity of source conduits for holding therein a sample and receiving therethrough the selected spectrum transmitted by said one of said multiplicity of source conduits; and detection and display means for receiving said selected spectrum transmitted through each of said multiplicity of sample cuvettes and detecting and displaying the transmission effects of the sample in each cuvette on said selected spectrum passed therethrough, said detection and display means being connected to said means for rotating said source filter wheel to synchronize and coordinate said display with the sequence of filter wheel filters.

2. The spectrophotometer described in claim 1 wherein said optical means includes:

a parabolic mirror having said single radiant energy source substantially located at the focal point thereof;

a lens mounting disk located in front of said parabolic mirror adjacent said filter wheel having a multiplicity of lens openings therethrough equally spaced from the axis of said parabolic mirror and circularly arranged therearound; and a multiplicity of lenses mounted in said multiplicity of lens openings of said lens mounting disk, for collecting radiant energy reflected by said parabolic mirror and directing said radiant energy through said filters of said filter wheel and into said multiplicity of source radiant energy conduits.

3. The spectrophotometer described in claim 2 wherein said lenses are plano-convex.

4. The spectrophotometer described in claim 1 wherein said detector and display means include:

a multiplicity of detector radiant energy conduits each having one end oppositely disposed one of said multiplicity of sample cuvettes to receive therefrom the selected spectrum of electromagnetic energy passed therethrough and to transmit said spectrum to the other end of said each detector conduit;

a detector filter wheel connected to said means for rotating said source filter wheel and having a given arrangement and sequence of filters, said detector radiant energy conduits being arranged such that a given filter of said detector filter wheel receives the spectral energy transmitted by a given filter of said source filter wheel;

a multiplicity of radiant energy detectors for converting the radiant energy falling thereon to electrical signals, each of said multiplicity of radiant energy detectors being located adjacent said detector filter wheel and oppositely disposed one of said multiplicity of detector radiant energy conduits such that as said detector filter wheel rotates the selected spectral radiant energy exiting from each of said multiplicity of detector radiant energy conduits passes through the corresponding filter on said detector filter wheel and into a radiant energy detector; and electronic means for processing the electrical signals from said multiplicity of radiant energy detectors for analyzing and displaying the transmission effects of each sample cuvette in response to the selected spectra passed therethrough.

5. The spectrophotometer described in claim 4 further including a blank segment in each of the source and detector filter wheels and further including a holding amplifier and means for gating the voltage offset appearing in a particular channel when said filter wheel blank segments appear in that channel to said holding amplifier such that any voltage offset which appears in that channel when the filter blanks are positioned in that channel, is detected, gated and held to be applied as an input to that channel to reduce the voltage offset of that channel to substantially a true zero.

6. The spectrophotometer described in claim 4 further including an automatic gain control circuit comprising:

a gate which is operated to transmit the amplitude of a first few of the train signal pulses in a particular channel to a capacitor;

a capacitor to hold the value of these pulse amplitudes;

an operational amplifier having an input connected to the capacitor and an output coupled to an optical coupler;

an optical coupler connected to a high voltage control;

a high voltage control connected to a high voltage supply; and a high voltage supply for a photomultiplier detector.

7. The spectrophotometer described in claim 4 wherein in said source and detector filter wheels have the same identical arrangement and sequence of filters such that a given filter of said detector filter wheel receives the spectral energy transmitted by the same identical filter of said source filter wheel.

8. The spectrophotometer described in claim 4 wherein said detector filter wheel is not identical to said source filter wheel and contains filters which are not the same as the filters of said source filter wheel whereby the sample cuvette can be excited by electromagnetic radiation at one wavelength and the fluorescent response thereto measured at another wavelength.

9. A Multichannel Spectrophotometer, comprising:
a single source of radiant energy;
optical means for forming said single source into a multiplicity of beams of radiant energy;
a first filter wheel adjacent said optical means and having a multiplicity of filter segments thereon, each filter segment intercepting one at a time each of said multiplicity of beams of radiant energy as the filter wheel rotates, each of said filter segments defining a band of spectral radiant energy;
means for transmitting each band of spectral radiant energy received from each filter segment to a measurement station;
a multiplicity of measurement stations each having a cuvette containing a sample to be measured by passing the spectral radiant energy received from said first filter wheel therethrough;
means for transmitting the radiant energy output received from each measurement station to a second filter wheel; and
a second filter wheel identical to said first filter wheel each filter segment intercepting one at a time each radiant energy output from said measurement stations, said second filter wheel being rotated in aligned synchronism with said first filter wheel such that a given band of spectral radiant energy transmitted through a given filter of said first filter wheel is received and transmitted through the same filter of said second filter wheel.

10. A multichannel spectrophotometer including optics for forming a multiplicity of radiant energy beams, comprising:
a parabolic reflector;
a source of radiant energy mounted at the focal point of said parabolic reflector;
a series of light baffles having a circular pattern of a multiplicity of circular holes therearound aligned and centered abut the axis of said parabolic reflector;
a lens disk adjacent to said light baffles having a multiplicity of circular lens assemblies aligned with said circular pattern of circular holes in said light baffles, each of said lens assemblies having a lens therein for forming a beam of radiant energy therefrom, said lens disk thereby providing a multiplicity of radiant energy beams therefrom; and,
a source filter wheel, having a multiplicity of spectrally selective filters arranged in a circular pattern substantially matching the circular pattern of lens within said lens disk, said source filter wheel and said filters thereon being positioned and arranged so that each filter sequentially receives and selectively transmits spectral portions of each one of said beams of radiant energy from said lens assembly as said source filter wheel is rotated.

* * * * *